United States Patent
Hu et al.

(10) Patent No.: US 9,662,349 B2
(45) Date of Patent: May 30, 2017

(54) **DIETARY COMPOSITION HAVING MIXED POLYSACCHARIDES DERIVED FROM LUCID *GANODERMA*, *LYCIUM BARBARUM* AND *POLYGONATUM SIBIRICUM* AND METHOD OF ITS PREPARATION**

(71) Applicant: Infinitus (China) Company Ltd., Jiangmen (CN)

(72) Inventors: Minghua Hu, Guangzhou (CN); Fangli Ma, Guangzhou (CN); Peipei Wang, Guangzhou (CN); Ming Liang, Guangzhou (CN)

(73) Assignee: Infinitus (China) Company Ltd., Jiangmen, Guangdong (CN)

( * ) Notice: Subject to any disclaimer, the term of this patent is extended or adjusted under 35 U.S.C. 154(b) by 0 days.

(21) Appl. No.: 14/615,442

(22) Filed: Feb. 6, 2015

(65) Prior Publication Data
US 2015/0366896 A1 Dec. 24, 2015

(30) Foreign Application Priority Data

Jun. 19, 2014 (CN) .......................... 2014 1 0273728

(51) Int. Cl.
*A61K 36/00* (2006.01)
*A61K 31/715* (2006.01)
*A61K 36/074* (2006.01)
*A61K 36/815* (2006.01)
*A61K 36/8969* (2006.01)

(52) U.S. Cl.
CPC .......... *A61K 31/715* (2013.01); *A61K 36/074* (2013.01); *A61K 36/815* (2013.01); *A61K 36/8969* (2013.01); *A61K 2236/00* (2013.01)

(58) Field of Classification Search
None
See application file for complete search history.

(56) References Cited

FOREIGN PATENT DOCUMENTS

CN 101991772 A * 3/2011
CN 102743754 A * 10/2012

* cited by examiner

*Primary Examiner* — Qiuwen MI
(74) *Attorney, Agent, or Firm* — Bei & Ocean; George G. Wang

(57) ABSTRACT

The present invention discloses a Lucid *Ganoderma*, *Lycium barbarum* and *Polygonatum sibiricum* complex polysaccharide having efficacy for regulating tumor microenvironment, whose active components are complexed by Lucid *Ganoderma* polysaccharide, *Lycium barbarum* polysaccharide and *Polygonatum sibiricum* polysaccharide, the mass proportion ratio of each component is Lucid *Ganoderma* polysaccharide 10-250, *Lycium barbarum* polysaccharide 1-50, *Polygonatum sibiricum* polysaccharide 2-10. The Lucid *Ganoderma*, *Lycium barbarum* and *Polygonatum sibiricum* complex polysaccharide is high in purity and activity, has an efficacy for regulating tumor microenvironment. The present invention also discloses the preparation method of aforesaid Lucid *Ganoderma*, *Lycium barbarum* and *Polygonatum sibiricum* complex polysaccharide, said method is simple, stable and efficient in the process, suitable for industrial production and economic. In addition, the present invention further discloses the use of aforesaid Lucid *Ganoderma*, *Lycium barbarum* and *Polygonatum sibiricum* polysaccharide in the preparation of health-care food having efficacy for regulating tumor microenvironment.

10 Claims, No Drawings

DIETARY COMPOSITION HAVING MIXED POLYSACCHARIDES DERIVED FROM LUCID *GANODERMA*, *LYCIUM BARBARUM* AND *POLYGONATUM SIBIRICUM* AND METHOD OF ITS PREPARATION

FIELD OF THE INVENTION

The present invention relates to the technical field of polysaccharide, specifically relating to a Lucid *Ganoderma*, *Lycium barbarum* and *Polygonatum sibiricum* complex polysaccharide having efficacy for regulating tumor microenvironment and preparation method and use thereof.

BACKGROUND OF THE INVENTION

Tumor recurrence and metastasis are the difficulties having universal significance in clinical tumor therapy, the reason is in that the target of current therapy is still focused on tumor cell per se, while the importance of its microenvironment is ignored. Tumor microenvironment and tumor cells are in a relationship of soil and seeds, the tumor malignancy process is a co-evolution process of tumor cells and microenvironment thereof, whose result is the wake-up of dormant tumor cells, entry into speed proliferation and metastasis. Therefore, improving tumor microenvironment, maintaining dormant status of tumor cells, is the current R&D focus and hotspot. Researches in recent years discover that, polysaccharide has a significant anti-tumor activity and has a rather small toxic side effect on human body, the study on the biological activity of polysaccharide has become the hotspot of research of experts and scholars at home and abroad in the medical field. Recent years, some polysaccharides and complex thereof are discovered as having significant efficacies on many diseases, such as immune disorders, cancer, diabetes, hypertension, hepatitis, blood clots, pneumonia, virus, and involving to the regulation of various living phenomena in the cell, and having effects for regulating tumor microenvironment.

Lucid *Ganoderma* is originally grown in Eastern Asia, the most broadly distributed province in China is Jiang'xi, Lucid *Ganoderma* being Chinese traditional precious medicinal material having thousands of years of medicinal history, having a very high medicinal value, as proved by tens of years of modern pharmacological study of scientific institution, Lucid *Ganoderma* has significant efficacy on each aspect of enhancing human body immunity, regulating blood glucose, controlling blood pressure, supplementing for tumor radio-chemotherapy, liver protecting and tonic, promoting sleeping. *Lycium barbarum* is a precious medicinal material and tonic, Traditional Medicine has a saying of "*Lycium barbarum* cultivates health" long ago. According to Compendium of Materia *Medica*, "*Lycium barbarum*, supplementing Kidney and generating Essence, Liver tonic . . . brightening Eyes and quieting the spirit, making one live long". *Polygonatum sibiricum* is a common traditional Chinese medicine, the rhizome of *Polygonatum sibiricum* is used as medicine. It has the functions of supplementing Qi and nourishing Yin, fortifying the Spleen, moistening the Lung, and tonifying the Kidney, is used for treating symptoms such as spleen-stomach vacuity, fatigued body and lack of strength, dry mouth and eat a little, Deficiency of Lung and cough due to dryness, insufficiency of Essence and Blood, inner heat of diabetes.

Nowadays, nobody uses Lucid *Ganoderma*, *Lycium barbarum* and *Polygonatum sibiricum* as raw material to extract polysaccharide and formulate into complex polysaccharide, and applied for the use of health-care food supplementary for inhibiting tumor.

SUMMARY OF THE INVENTION

The first technical problem to be solved by the present invention is to provide a Lucid *Ganoderma*, *Lycium barbarum* and *Polygonatum sibiricum* complex polysaccharide having efficacy for regulating tumor microenvironment, said complex polysaccharide has efficacy for regulating tumor microenvironment.

The second technical problem to be solved by the present invention is to provide the preparation method of aforesaid Lucid *Ganoderma*, *Lycium barbarum* and *Polygonatum sibiricum* complex polysaccharide having efficacy for regulating tumor microenvironment, said method is simple, stable and efficient in the process, suitable for industrial production and economic.

The third technical problem to be solved by the present invention is to provide the use of aforesaid Lucid *Ganoderma*, *Lycium barbarum* and *Polygonatum sibiricum* complex polysaccharide having efficacy for regulating tumor microenvironment in the preparation of health-care food having efficacy for regulating tumor microenvironment.

The first technical problem to be solved by the present invention is achieved by the following technical solution: a Lucid *Ganoderma*, *Lycium barbarum* and *Polygonatum sibiricum* complex polysaccharide having efficacy for regulating tumor microenvironment, whose active components are complexed by Lucid *Ganoderma* polysaccharide, *Lycium barbarum* polysaccharide and *Polygonatum sibiricum* polysaccharide, the mass proportion ratio of each component is Lucid *Ganoderma* polysaccharide 10-250, *Lycium barbarum* polysaccharide 1-50, *Polygonatum sibiricum* polysaccharide 2-10.

The mass proportion ratio of each raw material in the present invention is further preferably: Lucid *Ganoderma* polysaccharide 50-150, *Lycium barbarum* polysaccharide 20-40, *Polygonatum sibiricum* polysaccharide 4-8.

The mass proportion ratio of each raw material in the present invention is optimally: the mass proportion ratio of each component is Lucid *Ganoderma* polysaccharide 125, *Lycium barbarum* polysaccharide 10, *Polygonatum sibiricum* polysaccharide 4.

As a preferable embodiment of the present invention, the Lucid *Ganoderma* polysaccharide, *Lycium barbarum* polysaccharide or *Polygonatum sibiricum* polysaccharide of the present invention is prepared by the following method: Lucid *Ganoderma*, *Lycium barbarum* or *Polygonatum sibiricum* raw material is selected, and extracted with boiling water for many times, the extract liquid are combined and concentrated to obtain concentrate liquid a1, the concentrate liquid a1 is dialyzed with dialysis bag to obtain dialysate b1, dialysate b1 is concentrated to obtain concentrate liquid a2, trichloroacetic acid aqueous solution is added to concentrate liquid a2 to carry on protein precipitation followed by centrifugation, the supernatant is processed with neutralization, dialysis treatment to obtain dialysate b2, dialysate b2 is concentrated to obtain concentrate liquid a3, ethanol aqueous solution is added to the concentrate liquid a3 to carry on ethanol precipitation, the precipitate processed with drying treatment is Lucid *Ganoderma* polysaccharide, *Lycium barbarum* polysaccharide or *Polygonatum sibiricum* polysaccharide.

In the preparation process of the Lucid *Ganoderma* polysaccharide, *Lycium barbarum* polysaccharide or *Polygonatum sibiricum* polysaccharide of the present invention:

When extracted with boiling water, extraction is carried out for totally 1-5 times, the administration amount of boiling water during each extraction is 10-20 folds of the total mass of Lucid *Ganoderma*, *Lycium barbarum* or *Polygonatum sibiricum* raw material, the duration of each extraction is 4-5 h.

The volume percentage of trichloroacetic acid in the trichloroacetic acid aqueous solution is 15-35%, the administration amount thereof is the same as the volume of concentrate liquid a2, the duration of protein precipitation is 3-4 h.

The volume percentage of ethanol in the ethanol aqueous solution is 70-95%, the administration amount of ethanol aqueous solution is 2-4 folds of the total volume of concentrate liquid a3.

Dialysate b1 is preferably concentrated to around 1/10 of the original volume to obtain concentrate liquid a2, dialysate b2 is concentrated to around 1/10 of the original volume to obtain concentrate liquid a3.

The cutoff molecular weight of dialysis bag is about 3500 Da.

The second purpose of the present invention is achieved by the following technical solution: the preparation method of aforesaid Lucid *Ganoderma*, *Lycium barbarum* and *Polygonatum sibiricum* complex polysaccharide having efficacy for regulating tumor microenvironment, comprises the following steps:

(1) Lucid *Ganoderma*, *Lycium barbarum* or *Polygonatum sibiricum* raw material is selected, extracted with boiling water for many times, the extract liquid are combined and concentrated to obtain concentrate liquid a1;
(2) the concentrate liquid a1 is dialyzed with dialysis bag to obtain dialysate b1, dialysate b1 is concentrated to obtain concentrate liquid a2;
(3) trichloroacetic acid aqueous solution is added to concentrate liquid a2 to carry on protein precipitation followed by centrifugation, the supernatant is processed with neutralization, dialysis treatment to obtain dialysate b2, dialysate b2 is concentrated to obtain concentrate liquid a3;
(4) ethanol aqueous solution is added to the concentrate liquid a3 to carry on ethanol precipitation, the precipitate processed with drying treatment is Lucid *Ganoderma* polysaccharide, *Lycium barbarum* polysaccharide or *Polygonatum sibiricum* polysaccharide;
(5) Lucid *Ganoderma* polysaccharide, *Lycium barbarum* and *Polygonatum sibiricum* polysaccharide are mixed homogenously in the aforesaid stoichiometric ratio, i.e., Lucid *Ganoderma*, *Lycium barbarum* and *Polygonatum sibiricum* complex polysaccharide is prepared.

In the preparation method of the Lucid *Ganoderma*, *Lycium barbarum* and *Polygonatum sibiricum* complex polysaccharide: in Step (1), when extracted with boiling water, extraction is carried out for totally 1-5 times, the administration amount of boiling water during each extraction is preferably 10-20 folds of the total mass of Lucid *Ganoderma*, *Lycium barbarum* or *Polygonatum sibiricum* raw material, the duration of each extraction is preferably 4-5 h; in Step (3), the volume percentage of trichloroacetic acid in the trichloroacetic acid aqueous solution is preferably 15-35%, the administration amount thereof is preferably the same as the volume of concentrate liquid a2, the duration of protein precipitation is preferably 3-4 h; in Step (4), the volume percentage of ethanol in the ethanol aqueous solution is preferably 70-95%, the administration amount of ethanol aqueous solution is preferably 2-4 folds of the total volume of concentrate liquid a3.

In Step (3), dialysate b1 is preferably concentrated to around 1/10 of the original volume to obtain concentrate liquid a2, in Step (3), dialysate b2 is preferably concentrated to around 1/10 of the original volume to obtain concentrate liquid a3.

The cutoff molecular weight of dialysis bag in Step (2) and Step (3) is about 3500 Da.

The last purpose of the present invention is achieved by the following technical solution: the use of aforesaid Lucid *Ganoderma*, *Lycium barbarum* and *Polygonatum sibiricum* complex polysaccharide having efficacy for regulating tumor microenvironment in the preparation of health-care food having efficacy for regulating tumor microenvironment.

The dosage forms of the health-care food of the present invention can be capsule, tablet, powder, granule or oral liquid etc.

In view of the prior art, the present invention has the following advantages:

(1) the Lucid *Ganoderma*, *Lycium barbarum* and *Polygonatum sibiricum* complex polysaccharide of the present invention, can regulate tumor microenvironment by many pathways such as inhibiting tumor angiogenesis, immunosuppression and negative immunoregulation, it has good anti-tumore activity, can be orally administered directly, can also be formulated into many pharmaceutical dosage forms, such as capsule, tablet, powder, granule or oral liquid etc., after oral administration, it has efficacies of regulating tumor microenvironment and supplementary for inhibiting tumor;
(2) with Traditional Chinese medicinal herbs rich in active polysaccharide as the major material, the Lucid *Ganoderma*, *Lycium barbarum* and *Polygonatum sibiricum* complex polysaccharide of the present invention, by using a rational combination of various polysaccharide components, complexed for co-administration, regulates tumor microenvironment and supplementary for inhibiting tumor by many pathways, so it has a good effect on health-care of subhealth;
(3) the preparation method of the Lucid *Ganoderma*, *Lycium barbarum* and *Polygonatum sibiricum* complex polysaccharide of the present invention, said method is simple, stable and efficient in the process, suitable for industrial production and economic.

DETAILED DESCRIPTION OF PARTICULAR EMBODIMENTS OF THE INVENTION

The present invention will be further demonstrated by Examples hereinbelow, while the present invention is not restricted in any form.

All the raw materials used in the following Examples, if not specified, are commercially available products.

Part One Lucid *Ganoderma*, *Lycium barbarum* and *Polygonatum sibiricum* complex polysaccharide and preparation method thereof

Example 1

The Lucid *Ganoderma*, *Lycium barbarum* and *Polygonatum sibiricum* complex polysaccharide in this example, the active component thereof is complexed by Lucid *Ganoderma* polysaccharide, *Lycium barbarum* polysaccharide and *Polygonatum sibiricum* polysaccharide, wherein the mass proportion ratio of each component is Lucid *Ganoderma* polysaccharide 10, *Lycium barbarum* polysaccharide 50 and *Polygonatum sibiricum* polysaccharide 2.

The aforesaid Lucid *Ganoderma, Lycium barbarum* and *Polygonatum sibiricum* complex polysaccharide is prepared by the following method:

(1) preparation of Lucid *Ganoderma* polysaccharide: 3 kg of Lucid *Ganoderma* medicinal material is selected, 30 L of water is added, heated to boiling and extracted, totally extracted for 3 times, extracted for 5 h each time, the extract liquid are combined and concentrated to about 5 L to obtain concentrate liquid a1, concentrate liquid a1 is dialyzed against flowing water for about 2 d by using the dialysis bag (the cutoff molecular weight is 3500 Da, sic passim) to obtain dialysate b1, dialysate b1 is concentrated to 1/10 of the original volume to obtain concentrate liquid a2, the same volume of trichloroacetic acid aqueous solution is added to concentrate liquid a2 to perform protein precipitation followed by centrifugation, wherein the volume percentage of trichloroacetic acid in the trichloroacetic acid aqueous solution is 30%, at a temperature of 4° C., the duration of deproteinization is about 3-4 h, protein precipitate is removed, the supernatant is neutralized by sodium hydroxide aqueous solution (wherein the mass percentage content of sodium hydroxide is about 10%) to neutral to obtain neutral supernatant, the neutral supernatant is dialyzed (the cutoff molecular weight is 3500 Da, sic passim) for about 2 d to obtain dialysate b2, dialysate b2 is concentrated to about 3 L to obtain concentrate liquid a3, along with stirring, ethanol aqueous solution is added to the concentrate liquid a3 to carry on ethanol precipitation treatment, wherein the volume percentage of ethanol in the ethanol aqueous solution is 85%, the administration amount is about 3 folds of that of concentrate liquid a3, let stand for overnight, the precipitate is collected by centrifugation, the precipitate is dehydrated by dehydrate ethanol once, and dehydrated by acetone twice, respectively, vacuum dried at 40° C., the obtained precipitate is Lucid *Ganoderma* polysaccharide;

(2) preparation of *Lycium barbarum* polysaccharide and *Polygonatum sibiricum* polysaccharide, the preparation method is the same as that of Lucid *Ganoderma* polysaccharide;

(3) Lucid *Ganoderma* polysaccharide, *Lycium barbarum* polysaccharide and *Polygonatum sibiricum* polysaccharide are mixed homogenously in a mass proportion ratio of Lucid *Ganoderma* polysaccharide 10, *Lycium barbarum* polysaccharide 50 and *Polygonatum sibiricum* polysaccharide 2, i.e., the Lucid *Ganoderma, Lycium barbarum* and *Polygonatum sibiricum* complex polysaccharide is prepared.

Example 2

The Lucid *Ganoderma, Lycium barbarum* and *Polygonatum sibiricum* complex polysaccharide in this example, the active component thereof is complexed by Lucid *Ganoderma* polysaccharide, *Lycium barbarum* polysaccharide and *Polygonatum sibiricum* polysaccharide, wherein the mass proportion ratio of each component is Lucid *Ganoderma* polysaccharide 250, *Lycium barbarum* polysaccharide 1 and *Polygonatum sibiricum* polysaccharide 5.

The aforesaid Lucid *Ganoderma, Lycium barbarum* and *Polygonatum sibiricum* complex polysaccharide is prepared by the following method:

(1) preparation of Lucid *Ganoderma* polysaccharide: 3 kg of Lucid *Ganoderma* medicinal material is selected, 60 L of water is added, heated to boiling and extracted, totally extracted for 3 times, extracted for 4 h each time, the extract liquid are combined and concentrated to about 5 L to obtain concentrate liquid a1, concentrate liquid a1 is dialyzed against flowing water for about 2 d by using the dialysis bag) to obtain dialysate b1, dialysate b1 is concentrated to obtain concentrate liquid a2, the same volume of trichloroacetic acid aqueous solution is added to concentrate liquid a2 to perform protein precipitation followed by centrifugation, wherein the volume percentage of trichloroacetic acid in the trichloroacetic acid aqueous solution is 15%, at a temperature of 4° C., the duration of deproteinization is about 3-4 h, protein precipitate is removed, the supernatant is neutralized by sodium hydroxide aqueous solution (wherein the mass percentage content of sodium hydroxide is about 10%) to neutral to obtain neutral supernatant, the neutral supernatant is dialyzed for about 2 d to obtain dialysate b2, dialysate b2 is concentrated to about 3 L to obtain concentrate liquid a3, along with stirring, ethanol aqueous solution is added to the concentrate liquid a3 to carry on ethanol precipitation treatment, wherein the volume percentage of ethanol in the ethanol aqueous solution is 70%, the administration amount is about 3 folds of that of concentrate liquid a3, let stand for overnight, the precipitate is collected by centrifugation, the precipitate is dehydrated by dehydrate ethanol once, and dehydrated by acetone twice, respectively, vacuum dried at 40° C., the obtained precipitate is Lucid *Ganoderma* polysaccharide;

(2) preparation of *Lycium barbarum* polysaccharide and *Polygonatum sibiricum* polysaccharide, the preparation method is the same as that of Lucid *Ganoderma* polysaccharide;

(3) Lucid *Ganoderma* polysaccharide, *Lycium barbarum* polysaccharide and *Polygonatum sibiricum* polysaccharide are mixed homogenously in a mass proportion ratio of Lucid *Ganoderma* polysaccharide 250, *Lycium barbarum* polysaccharide 1 and *Polygonatum sibiricum* polysaccharide 5, i.e., the Lucid *Ganoderma, Lycium barbarum* and *Polygonatum sibiricum* complex polysaccharide is prepared.

Example 3

The Lucid *Ganoderma, Lycium barbarum* and *Polygonatum sibiricum* complex polysaccharide in this example, the active component thereof is complexed by Lucid *Ganoderma* polysaccharide, *Lycium barbarum* polysaccharide and *Polygonatum sibiricum* polysaccharide, wherein the mass proportion ratio of each component is Lucid *Ganoderma* polysaccharide 100, *Lycium barbarum* polysaccharide 20, *Lycium barbarum* polysaccharide 4.

The aforesaid Lucid *Ganoderma, Lycium barbarum* and *Polygonatum sibiricum* complex polysaccharide is prepared by the following method:

(1) preparation of Lucid *Ganoderma* polysaccharide: 3 kg of Lucid *Ganoderma* medicinal material is selected, 30 L of water is added, heated to boiling and extracted, totally extracted for 3 times, extracted for 5 h each time, the extract liquid are combined and concentrated to about 5 L to obtain concentrate liquid a1, concentrate liquid a1 is dialyzed against flowing water for about 2 d by using the dialysis bag to obtain dialysate b1, dialysate b1 is concentrated to obtain concentrate liquid a2, the same volume of trichloroacetic acid aqueous solution is added to concentrate liquid a2 to perform protein precipitation followed by centrifugation, wherein the volume percentage of trichloroacetic acid in the trichloroacetic acid aqueous solution is 35%, at a temperature of 4° C., the duration of deproteinization is about 3-4 h, protein precipitate is removed, the supernatant is neutralized by sodium hydroxide aqueous solution (wherein the mass percentage content of sodium hydroxide is about 10%) to neutral to obtain neutral supernatant, the neutral supernatant is dialyzed for about 2 d to obtain dialysate b2, dialysate b2 is concentrated to about 3 L to obtain concentrate liquid a3, along with stirring, ethanol aqueous solution is added to the concentrate liquid a3 to carry on ethanol precipitation treatment, wherein the volume percentage of ethanol in the ethanol aqueous solution is 80%, the administration amount is about 3 folds of that of concentrate liquid a3, let stand for overnight, the precipitate is collected by centrifugation, the precipitate is dehydrated by dehydrate ethanol once, and dehydrated by acetone twice, respectively, vacuum dried at 40° C., the obtained precipitate is Lucid *Ganoderma* polysaccharide;

(2) preparation of *Lycium barbarum* polysaccharide and *Polygonatum sibiricum* polysaccharide, the preparation method is the same as that of Lucid *Ganoderma* polysaccharide;

(3) Lucid *Ganoderma* polysaccharide, *Lycium barbarum* polysaccharide and *Polygonatum sibiricum* polysaccharide are mixed homogenously in a mass proportion ratio of Lucid *Ganoderma* polysaccharide 100, *Lycium barbarum* polysaccharide 20 and *Polygonatum sibiricum* polysaccharide 6, i.e., the Lucid *Ganoderma, Lycium barbarum* and *Polygonatum sibiricum* complex polysaccharide is prepared.

Example 4

The Lucid *Ganoderma, Lycium barbarum* and *Polygonatum sibiricum* complex polysaccharide in this example, the active component thereof is complexed by Lucid *Ganoderma* polysaccharide, *Lycium barbarum* polysaccharide and *Polygonatum sibiricum* polysaccharide, wherein the mass proportion ratio of each component is Lucid *Ganoderma* polysaccharide 150, *Lycium barbarum* polysaccharide 40 and *Polygonatum sibiricum* polysaccharide 6.

The aforesaid Lucid *Ganoderma, Lycium barbarum* and *Polygonatum sibiricum* complex polysaccharide is prepared by the following method:

(1) preparation of Lucid *Ganoderma* polysaccharide: 3 kg of Lucid *Ganoderma* medicinal material is selected, 60 L of water is added, heated to boiling and extracted, totally extracted for 5 times, extracted for 4 h each time, the extract liquid are combined and concentrated to about 5 L to obtain concentrate liquid a1, concentrate liquid a1 is dialyzed against flowing water for about 2 d by using the dialysis bag to obtain dialysate b1, dialysate b1 is concentrated to obtain concentrate liquid a2, the same volume of trichloroacetic acid aqueous solution is added to concentrate liquid a2 to perform protein precipitation followed by centrifugation, wherein the volume percentage of trichloroacetic acid in the trichloroacetic acid aqueous solution is 20%, at a temperature of 4° C., the duration of deproteinization is about 3-4 h, protein precipitate is removed, the supernatant is neutralized by sodium hydroxide aqueous solution (wherein the mass percentage content of sodium hydroxide is about 10%) to neutral to obtain neutral supernatant, the neutral supernatant is dialyzed (cutoff for about 2 d to obtain dialysate b2, dialysate b2 is concentrated to about 3 L to obtain concentrate liquid a3, along with stirring, ethanol aqueous solution is added to the concentrate liquid a3 to carry on ethanol precipitation treatment, wherein the volume percentage of ethanol in the ethanol aqueous solution is 80%, the administration amount is about 4 folds of that of concentrate liquid a3, let stand for overnight, the precipitate is collected by centrifugation, the precipitate is dehydrated by dehydrate ethanol once, and dehydrated by acetone twice, respectively, vacuum dried at 40° C., the obtained precipitate is Lucid *Ganoderma* polysaccharide;

(2) preparation of *Lycium barbarum* polysaccharide and *Polygonatum sibiricum* polysaccharide, the preparation method is the same as that of Lucid *Ganoderma* polysaccharide;

(3) Lucid *Ganoderma* polysaccharide, *Lycium barbarum* polysaccharide and *Polygonatum sibiricum* polysaccharide are mixed homogenously in a mass proportion ratio of Lucid *Ganoderma* polysaccharide 150, *Lycium barbarum* polysaccharide 40 and *Polygonatum sibiricum* polysaccharide 6, i.e., the Lucid *Ganoderma, Lycium barbarum* and *Polygonatum sibiricum* complex polysaccharide is prepared.

Example 5

The Lucid *Ganoderma, Lycium barbarum* and *Polygonatum sibiricum* complex polysaccharide in this example, the active component thereof is complexed by Lucid *Ganoderma* polysaccharide, *Lycium barbarum* polysaccharide and *Polygonatum sibiricum* polysaccharide, wherein the mass proportion ratio of each component is Lucid *Ganoderma* polysaccharide 100, *Lycium barbarum* polysaccharide 30, *Polygonatum sibiricum* polysaccharide 8.

The aforesaid Lucid *Ganoderma, Lycium barbarum* and *Polygonatum sibiricum* complex polysaccharide is prepared by the following method:

(1) preparation of Lucid *Ganoderma* polysaccharide: 3 kg of Lucid *Ganoderma* medicinal material is selected, 40 L of water is added, heated to boiling and extracted, totally extracted for 5 times, extracted for 5 h each time, the extract liquid are combined and concentrated to about 5 L to obtain concentrate liquid a1, concentrate liquid a1 is dialyzed against flowing water for about 2 d by using the dialysis bag to obtain dialysate b1, dialysate b1 is concentrated to obtain concentrate liquid a2, the same volume of trichloroacetic acid aqueous solution is added to concentrate liquid a2 to perform protein precipitation followed by centrifugation, wherein the volume percentage of trichloroacetic acid in the trichloroacetic acid aqueous solution is 35%, at a temperature of 4° C., the duration of deproteinization is about 3-4 h, protein precipitate is removed, the supernatant is neutralized by sodium hydroxide aqueous solution (wherein the mass percentage content of sodium hydroxide is about 10%) to neutral to obtain neutral supernatant, the neutral supernatant is dialyzed for about 2 d to obtain dialysate b2, dialysate b2 is concentrated to about 3 L to obtain concentrate liquid a3, along with stirring, ethanol aqueous solution is added to the concentrate liquid a3 to carry on ethanol precipitation treatment, wherein the volume percentage of ethanol in the ethanol aqueous solution is 95%, the administration amount is about 3 folds of that of concentrate liquid a3, let stand for overnight, the precipitate is collected by centrifugation, the precipitate is dehydrated by dehydrate ethanol once, and dehydrated by acetone twice, respectively, vacuum dried at 40° C., the obtained precipitate is Lucid *Ganoderma* polysaccharide;

(2) preparation of *Lycium barbarum* polysaccharide and *Polygonatum sibiricum* polysaccharide, the preparation method is the same as that of Lucid *Ganoderma* polysaccharide;

(3) Lucid *Ganoderma* polysaccharide, *Lycium barbarum* polysaccharide and *Polygonatum sibiricum* polysaccharide are mixed homogenously in a mass proportion ratio of Lucid *Ganoderma* polysaccharide 100, *Lycium barbarum* polysaccharide 30 and *Polygonatum sibiricum* polysaccharide 8, i.e., the Lucid *Ganoderma*, *Lycium barbarum* and *Polygonatum sibiricum* complex polysaccharide is prepared.

Example 6

The Lucid *Ganoderma*, *Lycium barbarum* and *Polygonatum sibiricum* complex polysaccharide in this example, the active component thereof is complexed by Lucid *Ganoderma* polysaccharide, *Lycium barbarum* polysaccharide and *Polygonatum sibiricum* polysaccharide, wherein the mass proportion ratio of each component is Lucid *Ganoderma* polysaccharide 200, *Lycium barbarum* polysaccharide 25, *Polygonatum sibiricum* polysaccharide 5.

The aforesaid Lucid *Ganoderma*, *Lycium barbarum* and *Polygonatum sibiricum* complex polysaccharide is prepared by the following method:
(1) preparation of Lucid *Ganoderma* polysaccharide: 3 kg of Lucid *Ganoderma* medicinal material is selected, 50 L of water is added, heated to boiling and extracted, totally extracted for 5 times, extracted for 4 h each time, the extract liquid are combined and concentrated to about 5 L to obtain concentrate liquid a1, concentrate liquid a1 is dialyzed against flowing water for about 2 d by using the dialysis bag to obtain dialysate b1, dialysate b1 is concentrated to obtain concentrate liquid a2, the same volume of trichloroacetic acid aqueous solution is added to concentrate liquid a2 to perform protein precipitation followed by centrifugation, wherein the volume percentage of trichloroacetic acid in the trichloroacetic acid aqueous solution is 20%, at a temperature of 4° C., the duration of deproteinization is about 3-4 h, protein precipitate is removed, the supernatant is neutralized by sodium hydroxide aqueous solution (wherein the mass percentage content of sodium hydroxide is about 10%) to neutral to obtain neutral supernatant, the neutral supernatant is dialyzed for about 2 d to obtain dialysate b2, dialysate b2 is concentrated to about 3 L to obtain concentrate liquid a3, along with stirring, ethanol aqueous solution is added to the concentrate liquid a3 to carry on ethanol precipitation treatment, wherein the volume percentage of ethanol in the ethanol aqueous solution is 80%, the administration amount is about 3 folds of that of concentrate liquid a3, let stand for overnight, the precipitate is collected by centrifugation, the precipitate is dehydrated by dehydrate ethanol once, and dehydrated by acetone twice, respectively, vacuum dried at 40° C., the obtained precipitate is Lucid *Ganoderma* polysaccharide;
(2) preparation of *Lycium barbarum* polysaccharide and *Polygonatum sibiricum* polysaccharide, the preparation method is the same as that of Lucid *Ganoderma* polysaccharide;
(3) Lucid *Ganoderma* polysaccharide, *Lycium barbarum* polysaccharide and *Polygonatum sibiricum* polysaccharide are mixed homogenously in a mass proportion ratio of Lucid *Ganoderma* polysaccharide 200, *Lycium barbarum* polysaccharide 25 and *Polygonatum sibiricum* polysaccharide 5, i.e., the Lucid *Ganoderma*, *Lycium barbarum* and *Polygonatum sibiricum* complex polysaccharide is prepared.

Example 7

The preparation method of Lucid *Ganoderma* polysaccharide, *Lycium barbarum* polysaccharide and *Polygonatum sibiricum* polysaccharide is the same as Example 10, Lucid *Ganoderma* polysaccharide 55 g, *Lycium barbarum* polysaccharide 5 g and *Polygonatum sibiricum* polysaccharide 1 g are respectively taken and mixed homogenously, to obtain complex polysaccharide component P1.

Example 8

The preparation method of Lucid *Ganoderma* polysaccharide and *Lycium barbarum* polysaccharide is the same as Example 1, Lucid *Ganoderma* polysaccharide 100 g, *Lycium barbarum* polysaccharide 15 g and *Polygonatum sibiricum* polysaccharide 1 g are respectively taken and mixed homogenously, to obtain complex polysaccharide component P2.

Example 9

The preparation method of Lucid *Ganoderma* polysaccharide and *Lycium barbarum* polysaccharide is the same as Example 1, Lucid *Ganoderma* polysaccharide 125 g, *Lycium barbarum* polysaccharide 10 g and *Polygonatum sibiricum* polysaccharide 4 g are respectively taken and mixed homogenously, to obtain complex polysaccharide component P3.

Example 10

Health-care food is prepared with the complex polysaccharide provided in the aforesaid Examples 1-9 as major effective component, by conventional process, it can be formulated into many pharmaceutical dosage forms, such as capsule, tablet, powder, granule or oral liquid etc.
Part Two Experiment of Polysaccharide and Complex Polysaccharide for Supplementary for Inhibiting Tumor Activity Example 11

Complex Polysaccharide can Inhibit the Activity of BRE Reporter Gene-Carrying Luciferase Induced by BMP2

C2C12 cell strain is purchased from the cell bank of Chinese Academy of Science (CAS), C2C12-pGF1-BRE cell strain is constructed by Dingkan Lab in Shanghai Institute of Materia Medica, CAS, and conserved in liquid nitrogen. C2C12-pGF1-BRE cell is cultivated in the DMEM medium comprising 10% Gibco fetal bovine serum, placed in an incubator having a saturated humidity at 37° C. and comprising 5% $CO_2$ to be cultivated, is inoculated in a density of $1\times10^4$ cell/well into a 96-well plate, 100 μL each well. After attaching for 24 h, 60 μL of medium is sucked, and replaced by 50 μL of polysaccharide sample (P1, P2, P3) prepared to be corresponding concentration, with a final concentration of 0.5 mg/mL, 0.1 mg/mL, 0.02 mg/mL, respectively, 10 μL of BMP2 is added to adjust to the final concentration of 200 ng/mL. Meanwhile, Blank group and BMP2 control group are set. After an administration of 16 h, medium is sucked, and replaced by 20 μL of Reporter Lysis 1× Buffer, 20 μL of the lysis solution of lytic cells is transferred to blank plate, 40 μL luciferase substrate is added, the plate is read in 3 min, RLU value is obtained. Statistical analysis is processed using SPSS statistical software. Each data is represented by mean±standard deviation (.x±s), the comparison between two groups is carried out by independent sample t test, the comparison among many groups is carried out by one-way ANOVA.

Example 12

Complex Polysaccharide on the Activity of Luciferase of NF-κB Reporter Gene

THP-1 cell strain is purchased from the cell bank of CAS, THP-1/pGF1-NF-κB cell strain is constructed by Dingkan Lab in Shanghai Institute of Materia Medica, CAS, and conserved in liquid nitrogen. THP-1/pGF1-NF-κB cell is cultivated in the RPMI-1640 medium comprising 10% fetal bovine serum, placed in an incubator having a saturated humidity at 37° C. and comprising 5% $CO_2$ to be cultivated, is inoculated in a density of $5\times10^4$ cell/well into a 96-well plate, a volume of 50 μL each well. 50 μL of test samples (P1, P2, P3) is added, with a final concentration of 0.5 mg/mL, 0.1 mg/mL, 0.02 mg/mL, respectively, Meanwhile, Blank group and LPS control group are set. 10 μL of LPS solution is added, to a final concentration of 1 μg/mL, and placed in an incubator having a saturated humidity at 37° C. and comprising 5% $CO_2$ to be cultivated overnight. After overnight cultivation, 100 μL of Bright-Glo™ Luciferase Assay System substrate is added to each well, the plate is read on a microplate reader, RLU value is obtained.

$$\text{Activation rate}(\%) = \frac{RLU(LPS) - RLU(\text{Compound})}{RLU(LPS) - RLU(\text{Blank})} \times 100\%$$

Statistical analysis is processed using SPSS statistical software. Each data is represented by mean±standard deviation (.x±s), the comparison between two groups is carried out by independent sample t test, the comparison among many groups is carried out by one-way ANOVA.

Example 13

Complex Polysaccharide can Inhibit the Activity Caused by Mouse S180 Transplanted Tumor Experimental animal: ICR mouse, 6-week age, female, body weight of 20±1 g, is purchased from Shanghai SLAC corporation.
a) S180 cell is thawed, cultivated in RPMI 1640+10% FBS for 2 generations, then cells are collected, resuspended in PBS to $1-2\times10^6$ cells/0.2 ml/mouse, intraperitoneal injected (i.p.) inoculation.
b) After the abdomen of the first generation breeding mouse is observed as rather huge (generally about 8-9 d), passage can be carried out. During passage, 1 ml syringe is taken, after disinfecting the abdomen of breeding mouse, the needle is directly inserted to suck ascitic fluid, note that the syringe should not be inserted too deep, as shallow as possible, the mouse can be lifted, by means of gravity, to make the ascitic fluid concentrated in a certain place to facilitate sucking, generally sucking 0.5 mL is fine, note that ascitic fluid should be placed on ice, unnecessary to be centrifuged, after directly diluted 3-6 folds by physiological saline, it is inoculated to the peritoneal cavity of another mouse, the ascitic fluid in a color of white or slightly yellowish is normal, while bloody ascitic fluid implies malignant, note it should be adjusted. After the second generation, had better passage on Day 6-7, but duration is better not too long, otherwise, ascitic fluid is easy to become bloody, after three generation, it can be used for experiment.

c) When experiment is started on Day 0, the required amount of sucked ascitic fluid is rather huge, once breeding mouse is sacrificed, the skin on abdomen is torn open with disinfecting ophthalmonogical scissors and forceps carefully, note that muscle should not be hurt, then, the muscle of abdomen is lifted with forceps, a tiny cut is cut with scissors, then ascitic fluid is sucked with glass drop dispenser or the syringe with needle removed. Then after certain dilution (generally 1:1-1:4, cell concentration is between $1-5\times10^7$ cells/mL), inoculated to the armpit of mouse. After 24 h of axillarily inoculation, mice are divided into groups randomly, 6 for each group, i.p. with different dosage of polysaccharide solution (P1, P2, P3), meanwhile, solvent group and positive medicine CTX group are set, the administration continues for 10 d, once daily.
d) Experiment is over on Day 11, mouse is sacrificed by breaking neck, the tumor is detached, the tumor and lymph organ are weighed, lymph organ index is calculated:

index of lymph organ=weight of lymph organ g/100×body weight g.

Data processing is carried out by OriginPro 8 or Graph-Pad Prism 4 software. The comparison between two groups of data is carried out by t-test and Two-way ANOVO, while the statistical analysis of comparison among many groups is carried out by one-way ANOVA. $p<0.05$ indicates a statistical significance.

Lucid *Ganoderma* polysaccharide, *Lycium barbarum* polysaccharide and *Polygonatum sibiricum* polysaccharide are formulated into complex polysaccharide in different ratios, the assay result of the biological activity of said complex polysaccharide for regulating tumor microenvironment is shown in Tables 1, 2 and 3. The results show that, the complex polysaccharide formulated by Lucid *Ganoderma* polysaccharide, *Lycium barbarum* polysaccharide and *Polygonatum sibiricum* polysaccharide in 3 different ratios, at a concentration of 0.5 mg/ml, has the biological activity of inhibiting angiogenesis, immune activation and inhibiting the growth of mouse S180 transplanted tumor at the same time. The combination of three or two polysaccharides, upon effective optimization, optimal ratio is obtained and complexed combination is made, when the mass ratio of Lucid *Ganoderma* polysaccharide, *Lycium barbarum* polysaccharide and *Polygonatum sibiricum* polysaccharide is Lucid *Ganoderma* polysaccharide 125 g, *Lycium barbarum* polysaccharide 10 g and *Polygonatum sibiricum* polysaccharide 4 g, in a polysaccharide concentration of 10 mg/kg, it has the best effect of anti-tumor activity, supplementation of medicine is carried on through combination, thus therapeutic effect can be improved significantly.

The aforesaid experiments prove that the polysaccharide complex can carry on the activity of regulating tumor microenvironment by many pathways such as inhibiting tumor angiogenesis, immune activation and inhibiting the growth of mouse transplanted tumor.

TABLE 1

The complex polysaccharide in 3 different ratios can inhibit the activity of BRE reporter gene-carrying luciferase induced by BMP2

| Sample name | P1 | | | P2 | | | P3 | | |
|---|---|---|---|---|---|---|---|---|---|
| concentration of sample (mg/ml) | 0.02 | 0.1 | 0.5 | 0.02 | 0.1 | 0.5 | 0.02 | 0.1 | 0.5 |

TABLE 1-continued

The complex polysaccharide in 3 different ratios can inhibit the activity of BRE reporter gene-carrying luciferase induced by BMP2

| Sample name | P1 | | | P2 | | | P3 | | |
|---|---|---|---|---|---|---|---|---|---|
| inhibition rate (%) | 17 | 28 | 55 | 18 | 29 | 49 | 27 | 48 | 76 |

TABLE 2

The complex polysaccharide in 3 different ratios can activate the activity of NF-κB reporter gene-carrying luciferase

| Sample name | P1 | | | P2 | | | P3 | | |
|---|---|---|---|---|---|---|---|---|---|
| concentration of sample (mg/ml) | 0.02 | 0.1 | 0.5 | 0.02 | 0.1 | 0.5 | 0.02 | 0.1 | 0.5 |
| Activation rate (%) | — | 6 | 14 | — | 3 | 7 | — | 7 | 21 |

TABLE 3

The complex polysaccharide in 3 different ratios can inhibit the growth of mouse S180 transplanted tumor

| Sample name | P1 | | | P2 | | | P3 | | |
|---|---|---|---|---|---|---|---|---|---|
| concentration of sample (mg/kg) | 5 | 10 | 50 | 5 | 10 | 50 | 5 | 10 | 50 |
| inhibition rate (%) | — | 32 | 15 | — | 24 | 10 | — | 53 | 27 |

The aforesaid examples are preferable embodiments of the present invention, but the embodiments of the present invention are not limited by the aforesaid examples, any other change, modification, substitution, combination, abbreviation made not departing from the spirit essence and principle of the present invention, is regarded as equivalent substitution manner, and are enclosed within the protection scope of the present invention.

What is claimed is:

1. A complex polysaccharide having efficacy for regulating tumor microenvironment, consisting of the Lucid *Ganoderma* polysaccharide, *Lycium barbarum* polysaccharide and *Polygonatum sibiricum* polysaccharide, wherein the mass proportion ratio of each polysaccharide is: Lucid *Ganoderma* polysaccharide 10-250, *Lycium barbarum* polysaccharide 1-50, *Polygonatum sibiricum* polysaccharide 2-10.

2. The complex polysaccharide having efficacy for regulating tumor microenvironment according to claim 1, wherein the mass proportion ratio of each polysaccharide is: Lucid *Ganoderma* polysaccharide 50-150, *Lycium barbarum* polysaccharide 20-40, *Polygonatum sibiricum* polysaccharide 4-8.

3. The complex polysaccharide having efficacy for regulating tumor microenvironment according to claim 2, wherein the mass proportion ratio of each polysaccharide is: Lucid *Ganoderma* polysaccharide 125, *Lycium barbarum* polysaccharide 10, *Polygonatum sibiricum* polysaccharide 4.

4. The complex polysaccharide having efficacy for regulating tumor microenvironment according to claim 1, wherein the Lucid *Ganoderma* polysaccharide, *Lycium barbarum* polysaccharide and *Polygonatum sibiricum* polysaccharide is prepared by the following method: Lucid *Ganoderma*, *Lycium barbarum* and *Polygonatum sibiricum* raw material are selected, extracted with boiling water for many times, the extract liquid are combined and concentrated to obtain concentrate liquid a1, the concentrate liquid a1 is dialyzed with dialysis bag to obtain dialysate b1, dialysate b1 is concentrated to obtain concentrate liquid a2, trichloroacetic acid aqueous solution is added to concentrate liquid a2 to carry on protein precipitation followed by centrifugation, the supernatant is processed with neutralization, dialysis treatment to obtain dialysate b2, dialysate b2 is concentrated to obtain concentrate liquid a3, ethanol aqueous solution is added to the concentrate liquid a3 to carry on ethanol precipitation, the precipitate processed with drying treatment.

5. The complex polysaccharide having efficacy for regulating tumor microenvironment according to claim 4, wherein when extracted with boiling water, extraction is carried out for totally 1-5 times, the administration amount of boiling water during each extraction is 10-20 folds of the total mass of Lucid *Ganoderma*, *Lycium barbarum* and *Polygonatum sibiricum* raw material, the duration of each extraction is 4-5 h.

6. The complex polysaccharide having efficacy for regulating tumor microenvironment according to claim 4, wherein the volume percentage of trichloroacetic acid in the trichloroacetic acid aqueous solution is 15-35%, the administration amount thereof is the same as the volume of concentrate liquid a2, the duration of protein precipitation is 3-4 h.

7. The complex polysaccharide having efficacy for regulating tumor microenvironment according to claim 4, wherein the volume percentage of ethanol in the ethanol aqueous solution is 70-95%, the administration amount of ethanol aqueous solution is 2-4 folds of the total volume of concentrate liquid a3.

8. The preparation method of the complex polysaccharide according to claim 1 comprising the following steps: (1) Lucid *Ganoderma*, *Lycium barbarum* and *Polygonatum sibiricum* raw material are selected, extracted with boiling water for many times, the extract liquid are combined and concentrated to obtain concentrate liquid a1;
   (2) the concentrate liquid a1 is dialyzed with dialysis bag to obtain dialysate b1, dialysate b1 is concentrated to obtain concentrate liquid a2;
   (3) trichloroacetic acid aqueous solution is added to concentrate liquid a2 to carry on protein precipitation followed by centrifugation, the supernatant is processed with neutralization, dialysis treatment to obtain dialysate b2, dialysate b2 is concentrated to obtain concentrate liquid a3;
   (4) ethanol aqueous solution is added to the concentrate liquid a3 to carry on ethanol precipitation, the precipitate processed with drying treatment is Lucid *Ganoderma* polysaccharide, *Lycium barbarum* polysaccharide or *Polygonatum sibiricum* polysaccharide;
   (5) Lucid *Ganoderma* polysaccharide, *Lycium barbarum* and *Polygonatum sibiricum* polysaccharide are mixed homogenously.

9. The preparation method according to claim 8, wherein: in Step (1), when extracted with boiling water, extraction is carried out for totally 1-5 times, the administration amount of boiling water during each extraction is 10-20 folds of the total mass of Lucid *Ganoderma, Lycium barbarum* or *Polygonatum sibiricum* raw material, the duration of each extraction is 4-5 h; in Step (3), the volume percentage of trichloroacetic acid in the trichloroacetic acid aqueous solution is 15-35%, the administration amount thereof is the same as the volume of concentrate liquid a2, the duration of protein precipitation is 3-4 h; in Step (4), the volume percentage of ethanol in the ethanol aqueous solution is 70-95%, the administration amount of ethanol aqueous solution is 2-4 folds of the total volume of concentrate liquid a3.

10. A method of regulating tumor microenvironment, said method comprising administering an effective amount of the complex polysaccharide according to claim 1 in the preparation of health-care food to a subject in need thereof.

* * * * *